(12) United States Patent
Badilini et al.

(10) Patent No.: US 7,424,137 B2
(45) Date of Patent: Sep. 9, 2008

(54) METHOD AND SYSTEM FOR CONVERTING PAPER ECG PRINTOUTS TO DIGITAL ECG FILES

(75) Inventors: Fabio F. Badilini, Brescia (IT); A. Tanju Erdem, Istanbul (TR)

(73) Assignee: A.M.P.S. L.L.C., New York, NY (US)

(*) Notice: Subject to any disclaimer, the term of this patent is extended or adjusted under 35 U.S.C. 154(b) by 928 days.

(21) Appl. No.: 10/831,531

(22) Filed: Apr. 23, 2004

(65) Prior Publication Data

US 2005/0027201 A1 Feb. 3, 2005

Related U.S. Application Data

(60) Provisional application No. 60/465,078, filed on Apr. 24, 2003.

(51) Int. Cl.
*G06K 9/00* (2006.01)

(52) U.S. Cl. .................................................. 382/128

(58) Field of Classification Search ................ 382/128
See application file for complete search history.

(56) References Cited

U.S. PATENT DOCUMENTS

| 6,580,817 | B2 * | 6/2003 | Badilini | 382/128 |
| 6,782,121 | B2 * | 8/2004 | Badilini | 382/128 |
| 7,181,054 | B2 * | 2/2007 | Zaleski | 382/128 |

* cited by examiner

*Primary Examiner*—Tom Y Lu
(74) *Attorney, Agent, or Firm*—Thomas R. FitzGerald; Hiscock & Barclay, LLP

(57) ABSTRACT

A method for digitizing a two-dimensional ECG chart includes scanning the ECG chart. The ECG chart includes an ECG waveform that appears on a background grid having generally horizontal and generally vertical grid lines. The background grid is detected, and the number of pixels between grid lines is determined. The vertical axis of the scanned ECG chart is scaled in units of volts per pixel and the horizontal axis of the scanned ECG chart is scaled in units of time per pixel.

20 Claims, 11 Drawing Sheets

METHOD AND SYSTEM FOR CONVERTING PAPER ECG PRINTOUTS TO DIGITAL ECG FILES

CROSS-REFERENCE TO RELATED APPLICATIONS

This application claims the benefit of U.S. Provisional Patent Application Ser. No. 60/465,078, filed 24 Apr. 2003.

FIELD OF THE INVENTION

The present invention relates to a method for deriving digital ECG waveforms from paper ECG charts/printouts and/or from ECG image files created by scanning such ECG paper charts/printouts.

BACKGROUND OF THE INVENTION

Electrocardiograms (ECGs) are widely used in clinical research to determine primary and secondary endpoints and, for example, to assess the effect of drug-induced relevant changes. The vast majority of such ECG analyses are performed either directly on paper ECG charts/printouts or using on-screen caliper methods applied to a displayed image of a scanned ECG paper chart/printout.

Advancements in technology are causing the health care industry as a whole to move increasingly toward the use of digital technologies. Digital technologies increase the efficiency with which data and images are stored, exchanged and analyzed. This general trend toward digital technologies is also being applied to ECGs. As an example, the Food and Drug Administration (FDA) has an initiative intended to encourage the use of digital ECGs in new drug applications submitted by pharmaceutical companies. Further, at least in part due to the predicted issuance of regulatory guidelines, there is likely to be a significant need for an efficient and widely acceptable method and system for the conversion of paper ECGs to digital ECGs.

The FDA initiative and predicted regulatory guidelines are likely to trigger the development of various tools for quantitative analysis of digital ECGs. For example, it is likely that the particular digital format chosen by the FDA for the submission of digital ECGs will be broadly adopted by the health care industry. Having a common or standardized digital ECG format will facilitate the interchange of ECG records among and between many entities.

Therefore, what is needed in the art is a method and system for deriving digital ECG waveforms from paper ECG charts/printouts and/or from ECG image files created by scanning such ECG paper charts/printouts.

SUMMARY OF THE INVENTION

The present invention provides a method for deriving digital ECG waveforms from paper ECG charts/printouts and/or from ECG image files created by scanning such ECG paper charts/printouts.

The present invention comprises, in one form thereof, a method that includes scanning an ECG chart that includes an ECG waveform appearing on a background grid having generally horizontal and generally vertical grid lines. The background grid is detected, and the number of pixels between grid lines is determined. The vertical axis of the scanned ECG chart is scaled in units of volts per pixel and the horizontal axis of the scanned ECG chart is scaled in units of time per pixel.

BRIEF DESCRIPTION OF THE DRAWINGS

The above-mentioned and other features and advantages of this invention, and the manner of attaining them, will become apparent and be better understood by reference to the following description of one embodiment of the invention in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION

Figure 1:
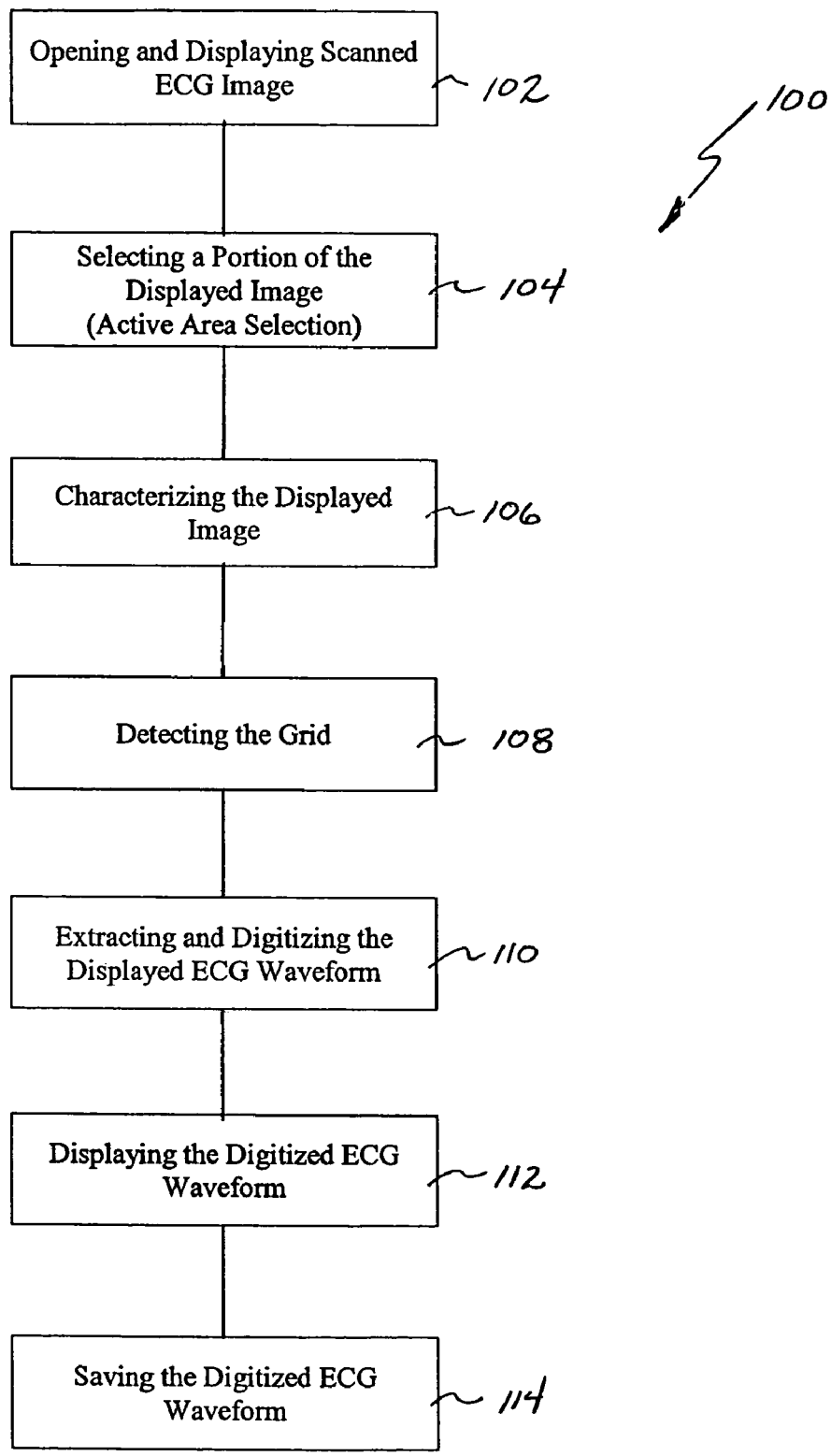
FIG. 1 shows one embodiment of a method of the present invention for deriving digital ECG waveforms from paper ECG charts/printouts and/or from ECG image files created by scanning such ECG paper charts/printouts.

With reference to the drawings, and particularly to FIG. 1, the method of the present invention includes the processes of opening and displaying scanned ECG image file 102, selecting a portion of the displayed image 104, characterizing the displayed image 106, detecting the grid 108, extracting and digitizing the ECG waveform 110, displaying the digitized ECG waveform 112, and saving the digitized ECG waveform 114.

Figure 2:
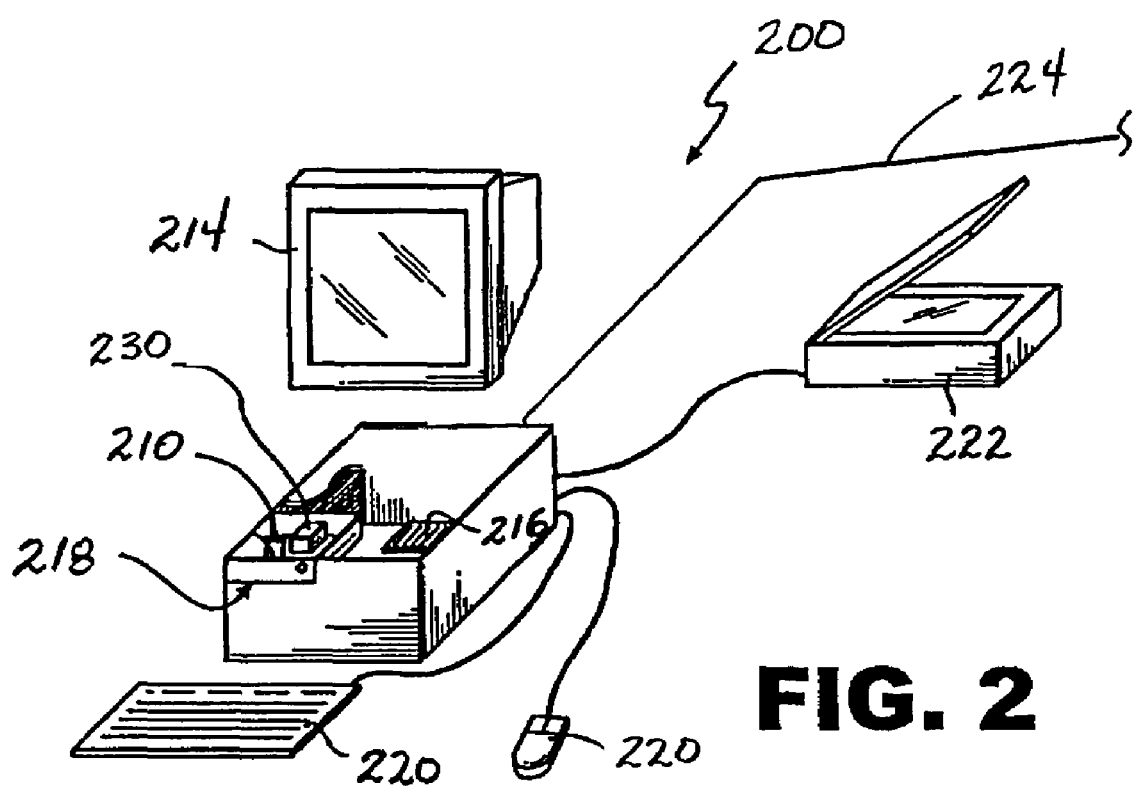
FIG. 2 shows one embodiment of a system of the present invention for deriving digital ECG waveforms from paper ECG charts/printouts and/or from ECG image files created by scanning such ECG paper charts/printouts.

Generally, and referring now to FIG. 2, method 100 is performed or carried out by system 200 executing application software 210. System 200 includes a computer 212, such as, for example, a conventional personal computer having a display 214, memory 216, one or more storage devices 218, one or more input devices 220, and optical scanner 222. Memory 216 includes random access memory and read only memory. Storage devices 218 are configured as, for example, one or more of a hard disk drive, removable memory card, or floppy disk drive. Input devices 220 include one or more of a keyboard, mouse, or other input device. Optical scanner 222 is a conventional optical scanner. Computer 212 is optionally connected to network 224 that enables the exchange of data, such as, for example, a local area network, wide area network, an intranet or the Internet.

ECG image file 230 is a computer-readable file that contains or embodies a scanned and bitmapped image of a paper ECG chart or printout. ECG image file 230 is preferably stored as or converted to one of several predetermined file formats, such as, for example, a bitmap (BMP) format, Joint Photograph Expert Group (JPEG) format, Graphics Interchange (GIF) format, Tagged Image (TIF) format, and Portable Network Graphic format (PNG). As shown in FIG. 2, image file 230 is stored in one of storage devices 218. However, it is to be understood that image file 230 can be stored in virtually any location so long as it is accessible to and can be retrieved by computer 212. Alternatively, image file 230 can be read directly from optical scanner 222.

Application software 210 embodies, at least in part, method 100. Application software 210 is stored in one of storage devices 218, and at least a portion thereof is read into memory 216 for execution by computer 212. Computer 212 executing application software 210 performs method 100, which is more particularly described hereinafter.

Opening and Displaying a Scanned ECG Image File 102

Opening and Displaying a scanned ECG image file 102 includes the process of accessing and opening ECG image file 230. Responsive to input from a user of system 200, such as, for example, via one of input devices 220, computer 212 executing application software 210 retrieves ECG image file 230 from its storage location. ECG image file 230, as discussed above, is preferably stored as or converted to one of several predetermined file formats, such as, for example, a bitmap (BMP) format, Joint Photograph Expert Group (JPEG) format, Graphics Interchange (GIF) format, Tagged Image (TIF) format, and Portable Network Graphic format (PNG).

Figure 3:
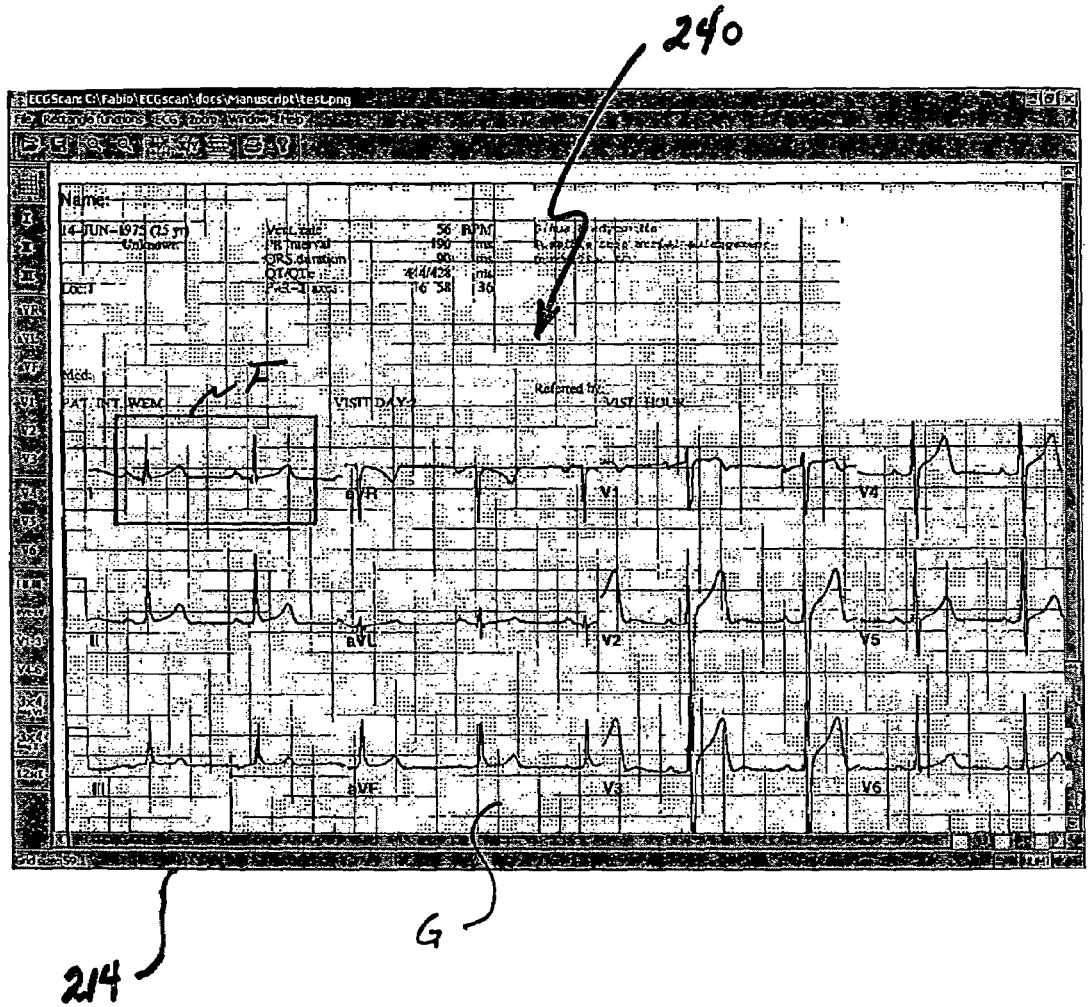
FIG. 3 shows a display of an ECG image file created by scanning a paper ECG chart or printout.

The retrieved ECG image file, as shown in FIG. 3, is displayed as ECG wave 240 on display 214. Displayed ECG wave 240 is a bitmapped display of the paper ECG chart or printout that was scanned to create ECG image file 230.

Selecting a Portion of the Displayed Image 104

Selecting a Portion of the Displayed Image 104 includes the selection, by default or based upon user input to system 200 via an input device 220, of a portion, such as a rectangular portion, of displayed ECG wave 240. The selected portion of displayed ECG wave 240, also referred to as the active area, is identified by a frame F which is also displayed on display 214 as shown in FIG. 3. The active area, which by default encompasses the entire displayed ECG wave 240, is manipulated and/or changed by a user actuating an input device 220.

Characterizing the Displayed Image 106

Figure 4:
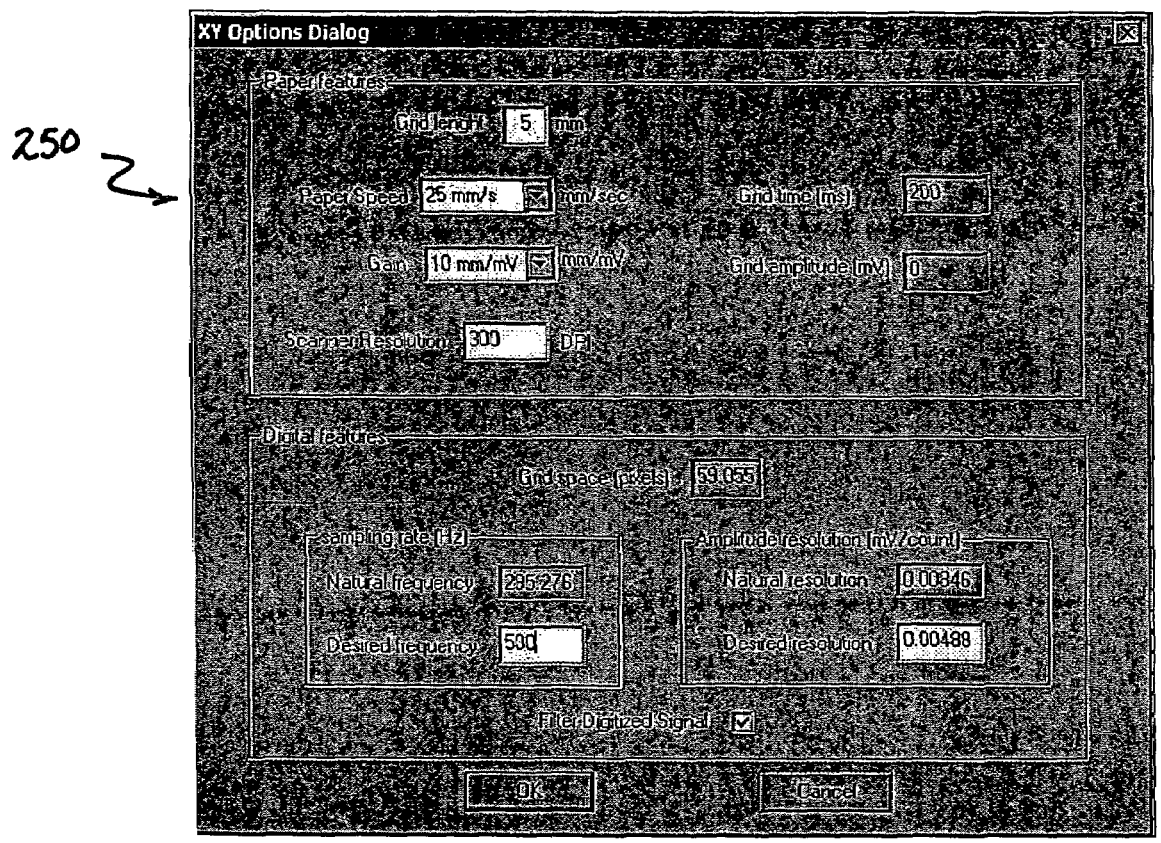
FIG. 4 shows a characterization dialog box for input and/or verification of certain parameters of a displayed ECG wave.

Characterizing the displayed image 106 includes verification of the characteristics and/or parameters of the ECG paper chart or printout that was scanned to form the ECG image file 230 and which is displayed as ECG wave 240. Computer 212 executing application software 210 displays an XY Options dialog box 250, shown in FIG. 4, for input and/or verification by a user of system 200 of certain parameters of ECG wave 240.

More particularly, in the "Paper features" group of dialog box 250 the parameters of paper speed and gain are either confirmed or set by the user to reflect the values that correspond to those of ECG image file 230 and/or displayed ECG wave 240. In the "Digital features" group of dialog box 250 the user sets the required levels for sampling rate (Hz) and amplitude resolution (mV/count) which by default are set to 500 Hz and 0.0025 mVolts/Count (400 counts×1 mV). The read-only values in the Natural Frequencies and Natural Resolution fields are those imposed by the resolution at which the ECG paper chart was scanned to create ECG image 230, and the fields correspond to the sampling rate and amplitude resolution intrinsic to the pixel spacing of ECG image file 230 and/or displayed ECG wave 240.

It should be noted that the output sampling rate and amplitude resolution do not necessarily have to match the corresponding "natural" levels. Application software 210 converts resamples and/or rescales to the proper levels.

Detecting the Grid 108

Displayed ECG wave 240 includes a grid G formed of a series of solid or dashed/dotted lines that corresponds to the grid of the original paper ECG chart or printout. The grid indicates the horizontal and vertical scale divisions of the image.

The process of detecting the grid G of displayed ECG image 240 is separate from the process of digitizing the waveform within the active area. The process of digitization (i.e., digitization process 110) is fully controlled by a dedicated docking toolbar which is, by default, placed at the left part of display 214, as will be more particularly described hereinafter.

The purpose of grid detection process 108 is to detect the exact position of grid G in displayed ECG image 240 in terms of pixel distance between grid lines and in terms of the angle of grid lines. Grid detection process 108 is conducted according to one of a manual mode, range mode and exact mode.

In the exact mode, the user of system 200 must know with certainty the input parameters of the paper ECG chart or printout from which ECG image file 230 and displayed ECG image 240 were created. More particularly, the paper speed used to create the original ECG paper chart or printout, the resolution at which the original ECG paper chart or printout was scanned, and the time distance between grid lines of the original ECG paper chart or printout must be known. When these quantities are known, the distance in pixel units between grid lines is derived mathematically by the formula:

$$\frac{\text{Pixels/grid}}{[\text{pixels/inch}]} = \frac{\text{grid time } [\text{sec/grid}] \times \text{paper speed } [\text{mm/sec}] \times \text{DPI}}{25.4 \, [\text{mm/inch}]}$$

For example, an ECG paper chart made with a paper speed of 25 mm/sec scanned at a scanner resolution of 300 DPI and having a grid time of 0.2 sec/grid will have 59.055 pixels between grid lines. The above formula is simplified by substituting the grid length in mm for the product of grid time and paper speed. Indeed, the concept of grid space is independent of how much time is represented in one grid box. The typical grid length is 5 mm and is obtained by multiplying paper speed and grid time. For example, at 25 mm/sec the grid time is 0.2 sec and at 50 mm/sec the grid time is 0.1 sec, and in both cases grid length is typically 5 mm. The exact mode of grid detection process 108 still applies the extended formula as the concept of paper speed is needed to map pixels to time samples during digitization process 110.

The range grid mode applies the same formula as is applied in the exact mode as described above. However, a user-selectable tolerance range on the exactness of the formula is assumed and grid detection process 108 re-detects grid G on the basis of that tolerance range. The range grid mode is particularly well suited to cases where the input features of the ECG paper chart and/or displayed ECG image 240 are known but some potential deviations from those features may exist, such as, for example, when a photocopy or a fax copy of an ECG paper chart was used/scanned to create ECG image file 230.

In the manual grid mode, grid G is detected without requiring a user to input any known features of displayed ECG image 240. In manual grid mode, the user selects, in the manner described above in regard to the process of selecting a portion of displayed image 104, an area of displayed ECG image 240 that includes at least approximately 4 to 5 grid sections in each of the horizontal and vertical directions. The grid lines of the selected area should be relatively clean, i.e., clear and distinct grid lines, but may contain portions of the ECG wave itself or other indicia, such as text. The detection algorithm eliminates non-repetitive elements, and thus it is preferable for a user to select an active area that contains the ECG waveform and relatively distinct grid lines rather than selecting an active area without the ECG waveform but having faded or discontinuous grid lines. Upon completion of grid detection process 108, a notification message is displayed on display 214 that indicates the estimated grid spacing (number of pixels between grid lines), grid angle (the presence of tilt in the grid lines and/or displayed ECG image 240) and the reliability of the grid detection process.

In the manual mode, computer 212 executing application software 210 counts the total number of pixels in the active/selected area and then divides the total number of pixels by the detected segments of grid G to yield the average number of pixels per grid section. The grid segments are detected by detecting the vertical and horizontal grid lines. The process of detecting the vertical and horizontal grid lines includes finding the spacing between two consecutive grid lines, the tilt of grid lines, and the offset of grid lines with respect to a specific location of the active area, such as, for example, the center of the active area. The darkness of the gridlines, the relatively even spacing thereof in both horizontal and vertical directions, their common tilt, and their uniformity (i.e., typically 4 minor/thin grid lines disposed between every two major/thick grid lines).

Extracting and Digitizing the ECG Waveform 110

The task of extracting the ECG waveform from displayed ECG wave 240 also utilizes the process of selecting a portion of the displayed image 104 as described above. The user of system 200, by selecting an appropriate active area, has the option to digitize a single lead, a group of leads, or the entirety of displayed ECG wave 240. The digitizing process 110 includes presenting to the user on display 214 a dedicated toolbar (shown in FIG. 3) that is activated once grid G has been detected. The digitizing toolbar has individual or simultaneous waveform detection options. A set of buttons correspond to each of the individual leads of displayed ECG image 240 and another group of buttons correspond to the selection of a group of leads for simultaneous digitization. The extracting and digitizing process 110 is configured for various digitization scenarios, including:

3×4 with one long V1 lead at the bottom

3×4 with one long lead II at the bottom

12×1, i.e. all 12 leads, one for each row

Displayed ECG wave 240 is digitized by extracting and digitizing process 110 using the concepts of active contours (also sometimes referred to as "snakes") and dynamic programming. The active contour model was first introduced by Kass, et al. (Kass M, Witkin A, Terzopoulos D., Snakes: Active Contour Models, *Int. Journal Computer Vision,* 1(4): 321-331, 1988) as a parametric waveform that minimizes a cost function defined in terms of the attributes of a digital image. A dynamic programming approach was first used by Amini et al. (Amini A A, Weymouth T E, Jain R C, Using Dynamic Programming for Solving Variational Problems in Vision, *IEEE Trans. PAMI,* 12(9), 885-867, 1990) to minimize the cost function, and hence to solve for the optimum waveform, via a numerical algorithm suitable for computer programming.

In the method of the present invention, a digital ECG waveform is represented by an active contour that has a vertical value or position corresponding to each horizontal pixel location within the active or selected area of the displayed ECG wave 240. The vertical value or position represents the voltage level and the horizontal location represents the time value of the displayed ECG wave 240. A cost function is defined for the displayed ECG wave 240 in such a way that the solution which minimizes the cost function corresponds to the desired digital representation of displayed ECG wave 240.

Figure 5:
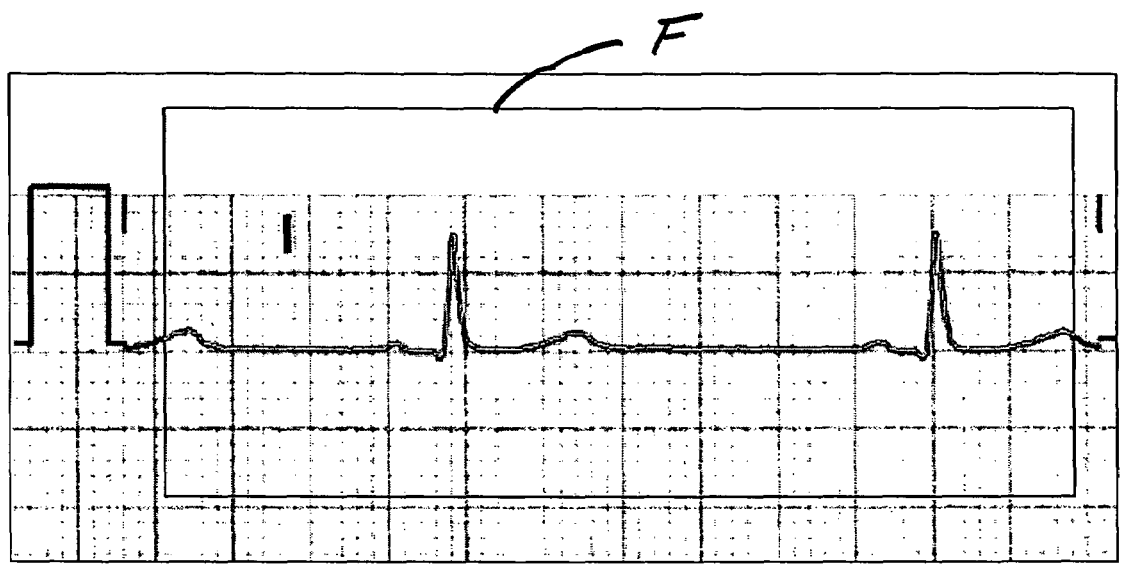
FIG. 5 shows an exemplary single-lead ECG waveform extraction.

The cost function is defined as a sum of several cost functions of different natures. A "line" cost function is used to attach the active contour to the ECG waveform on displayed ECG wave 240. A "smoothness" cost function is used to reduce discontinuities in the digitized ECG waveform. A "length" cost function is used so that the active contour approaches or reaches the end points of the maximum and minimum points of the ECG waveform on displayed ECG wave 240. Certain thresholds are applied in the definitions of these cost functions so that the digitized waveform is not attracted to extraneous lines, marks, or letters while avoiding the white or empty space on displayed ECG wave 240. FIG. 5 shows an example of a single lead waveform extraction.

The extracting and digitizing process 110 corrects for any tilt in the displayed ECG wave 240, and finds the vertical pixel location of the ECG waveform for every horizontal pixel location in the active area. It should be noted that the vertical pixel locations can assume fractional values. The horizontal and vertical pixel locations are converted into actual time and voltage values, respectively, based on the time and voltage scale of grid G.

The method of finding the vertical pixel location for every horizontal pixel location includes defining an active contour that has a control point for each and every horizontal pixel location in the active area, setting the horizontal locations of consecutive control points equal to the consecutive horizontal pixel locations in the active area, and "snapping" the active contour to the actual ECG waveform in the active area by moving only the vertical locations of the control points.

The method of "snapping" is an iterative process which aims to minimize a cost function within a search space. The cost function is defined in terms of the image color at a control point, the distance between two consecutive control points, and the angle between the two lines that connect a control point to the previous and next control points. The mathematical definition of the cost function in terms of the image color, the distance, and the angle values is such that the cost function is minimized when the active contour assumes the shape of the waveform. The search space for each iteration of the snapping process is defined in terms of the vertical location that the control points could assume while satisfying certain constraints. These constraints are in the form of maximum distance between two consecutive control points and/or are specified by the user of system 200 as vertical locations or a range of vertical locations for certain horizontal pixel locations.

Displaying the Digitized ECG Waveform 112

Figure 6:
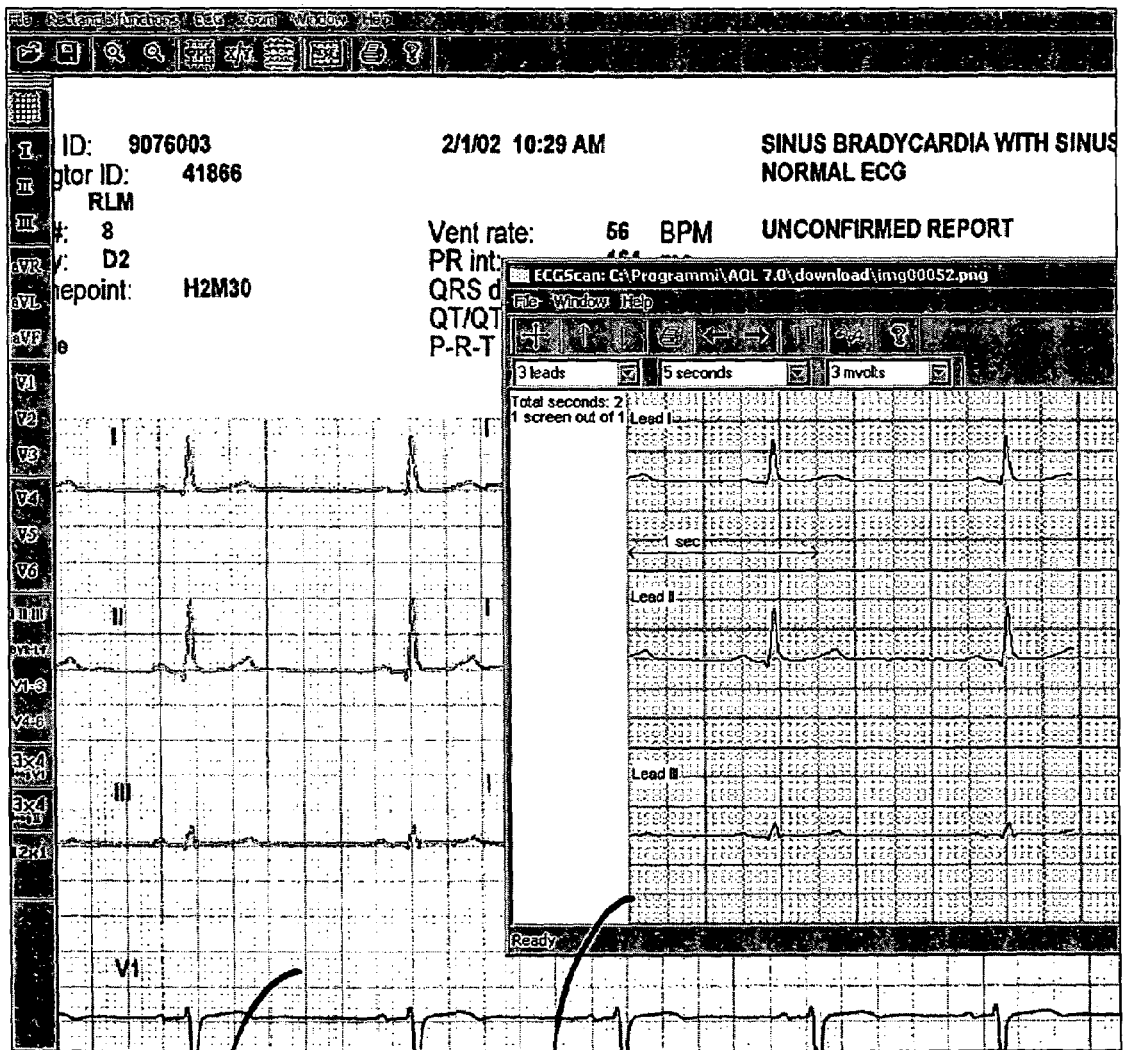
FIG. 6 shows an example of a display window within which is contained a digitized ECG wave.

The process of displaying the digitized ECG waveform 112 preferably includes, as best shown in FIG. 6, displaying digitized ECG waveform 244 in a dedicated window on display 214. The display organization of this window (i.e. how many seconds to show per lead, how many leads to display in one screen and in which order, which gain to use, etc) is set by the user, although application software 210 provides default values. The display of the digitized ECG waveform 244 ensures the user that the digitization process has performed adequately.

Saving the Digitized ECG Waveform 114

The digitized waveform is saved as a computer-readable file, such as, for example, in a storage device 218, in one of several user-selectable formats, such as, for example, XML, ASCII or binary.

Validation of the Method of the Present Invention

Clinical testing of the method of the present invention was performed for the purpose of determining how well a digitized ECG reflects an original digital ECG. Two separate tests were performed. The first test provided quantitative information of the actual voltage differences between original digital and derived digital ECGs. The method of the present invention was used to derive the digital ECGs. The second test compared semiautomatic measurements of QT intervals performed on original and on the derived/digitized ECG waveforms.

The dataset consisted of sixty 12 lead ECGs provided by University of Rochester (located in Rochester, N.Y.) Heart Research Follow-Up program. Thirty ECGs are from normal subjects whereas the remaining 30 are extracted from the international Long QT syndrome (LQTS) registry. The ECGs were acquired with a GEMSIT cart (MacView) and stored in digital format onto floppy disks. The same ECGs were also printed with a standard output mode (i.e., 25 mm/sec. 10 mm/mV, 3 by 4 display mode showing the first 2.5 seconds for each of the 12 leads, and with 10 seconds of one lead (V1) printed at the bottom).

The digital ECGs were extracted from floppy disks using the GEMSIT Magellan software package (available from Magellan ECG Research) which converts the digital ECGs into a standard binary format, inclusive of subject information and rhythm data saved at 250 samples per second with 4.88 microvolt resolution.

The paper ECG printouts were scanned (using an EPSON GT-7000) at a resolution of 300 DPI (dots per inch) using an 8-bit grayscale color depth. All scanned images were subsequently stored in a PNG (Portable Network Graphic) format (loss-less compression) for use as ECG image files 230 by method 100, which was then executed to digitize and thereby derive a set of digitized ECGs.

Figure 7:
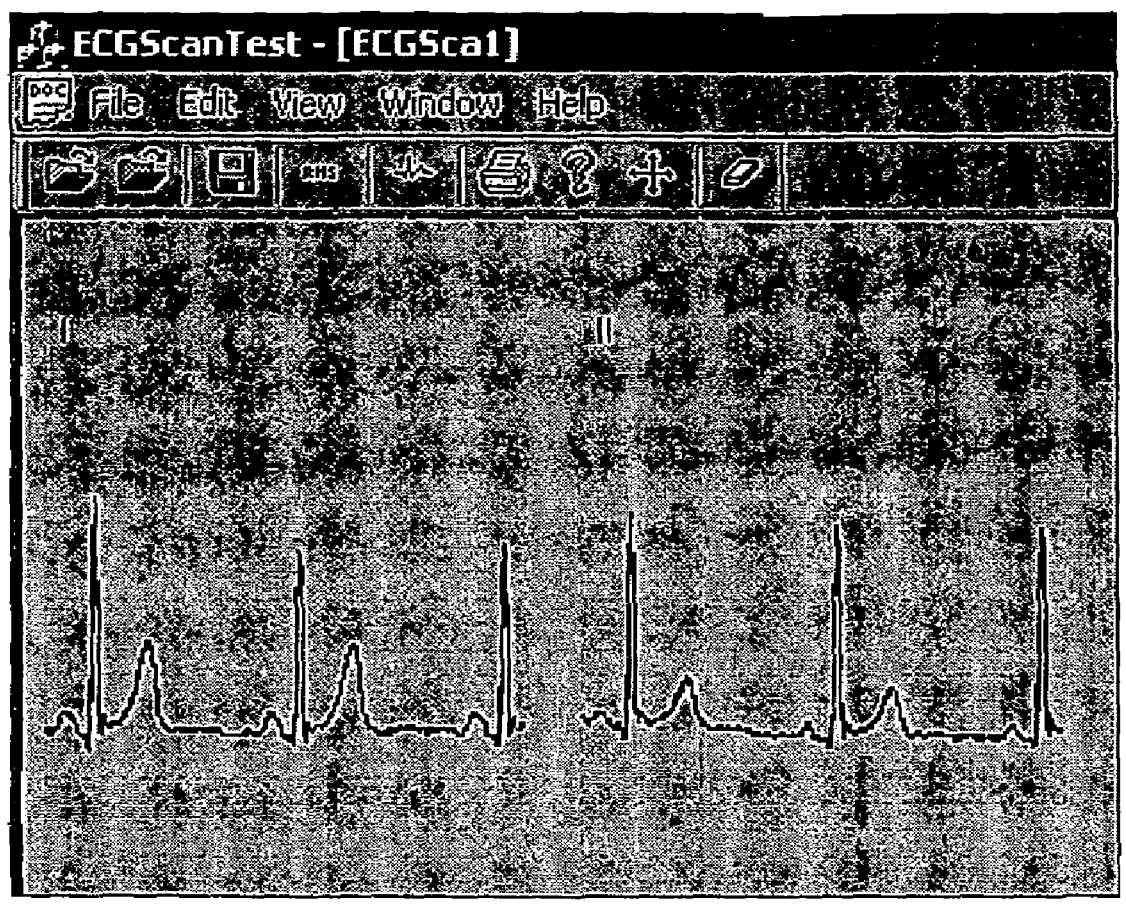
FIG. 7 is an example of a display showing a superimposition of the original and digitized ECG waveforms.

Quantitative assessment of the differences between the original and derived/digitized ECGs was conducted by simultaneously loading and displaying the ECGs. The lag (number of samples by which the two waves/sequences are shifted) between each independent lead was computed and numerical results in terms of quantitative differences between the original and digitized ECG and the QT intervals thereof were extracted. FIG. 7 shows an example of a display showing a superimposition of an original and a derived ECG waveform.

The grids of the scanned ECG waveforms were detected using grid detection process 108 in the range grid detection mode with a 10% range (i.e. knowledge of paper speed and scanning resolution, respectively 25 mm/sec and 300 dpi). For each displayed ECG image file, between 2 and 2.4 seconds of leads I, II and III were digitized according to method 100 and saved to an output ASCII file. The characteristics of the output signals were user-imposed to match those of the original digital ECGs, i.e. a sampling rate of 250 Hz and an output amplitude resolution of 4.88 microvolts.

For each digitized sequence the optimal lag and the mean and median value of the differences were determined. A least square fit analysis was run to inspect how closely the samples fit the ideal $y_i = x_i$ line (i.e. a perfect 45° line). Table 1 summarizes the results, wherein Mean$\Delta$ and Median$\Delta$ indicate the mean and median values of the sample-by-sample differences obtained for each ECG after taking into account the computed shift between the two signals. Mean values of both Mean$\Delta$ and Median$\Delta$ are well below the sampling interval (4 microvolts at 250 Hz).

TABLE 1

| n = 169 | Mean Δ | Median Δ | Slope | corr |
|---------|--------|----------|-------|------|
| Mean    | −1.37  | −0.32    | 0.977 | 0.95 |
| SD      | 4.29   | 4.56     | 0.04  | 0.03 |
| Min     | −14    | −9.76    | 0.78  | 0.86 |
| Max     | 9.2    | 9.76     | 1.08  | 0.99 |

Figure 8A:
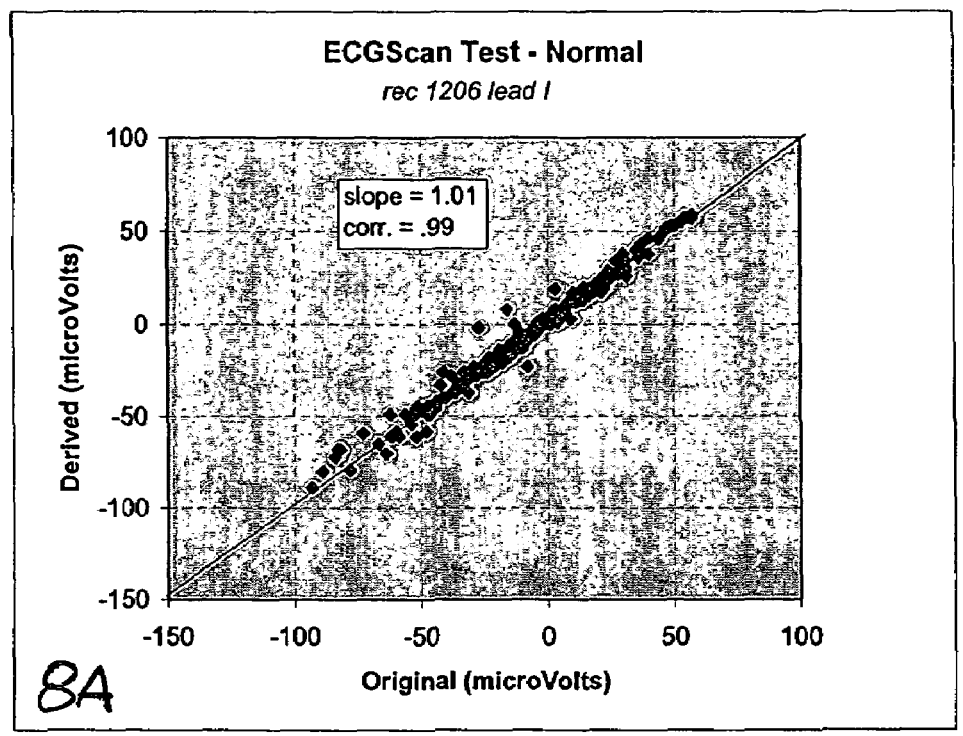
FIGS. 8A and 8B show exemplary linear fit analyses for the derived/digitized ECG waves of a normal subject and an LQTS patient, respectively.
Figure 8B:
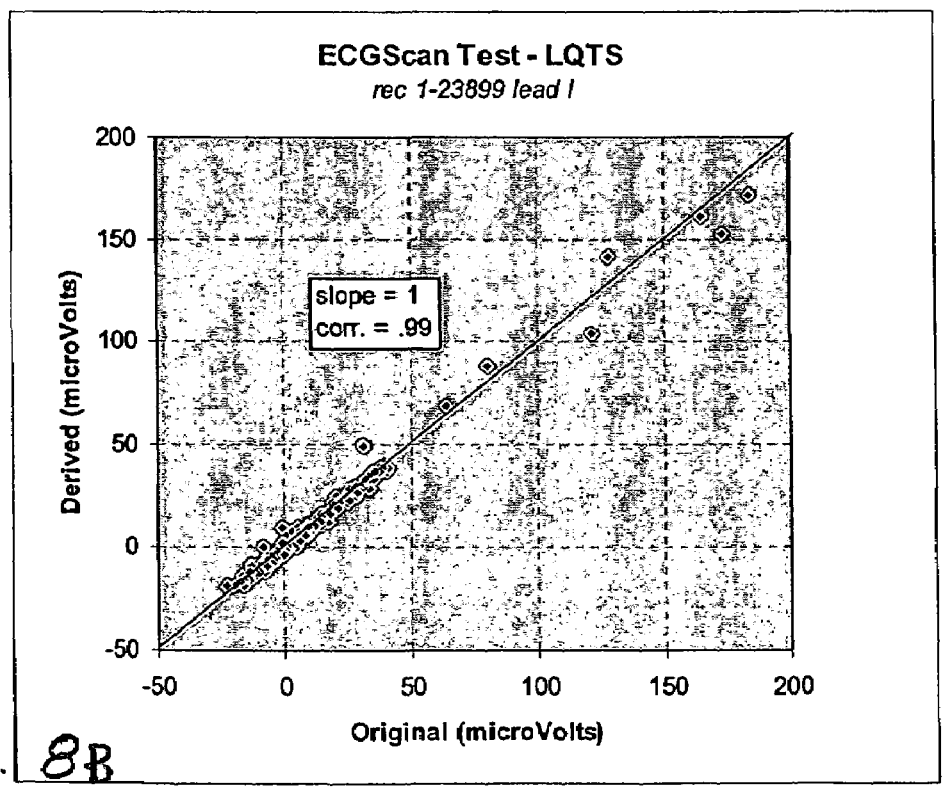

Results of the least-square best fit show that both correlation and slope of fit are very close to 1 with very narrow variations between ECGs (correlation absolute minimum is 0.86, and in only 2 cases out of 169 was the correlation below 0.90). FIGS. 8*a* and 8*b* are two representative examples of linear fit analysis for a normal subject and a LQTS patient, respectively. Both examples are run over 600 samples the observed pairs of derived/original samples are systematically close to the y=x line.

For each pair of original and derived digital ECGs (lead I, II and III) the user chose a time window containing the first complete PQRST complex available. The $Q_{ONSET}$ and $T_{OFFSET}$ calipers were computed using a previously published method that determines automatic measurements that are corrected, if necessary, by a user. Leads with flat T waves (less than 100 microvolts T peak) were excluded.

Figure 9:
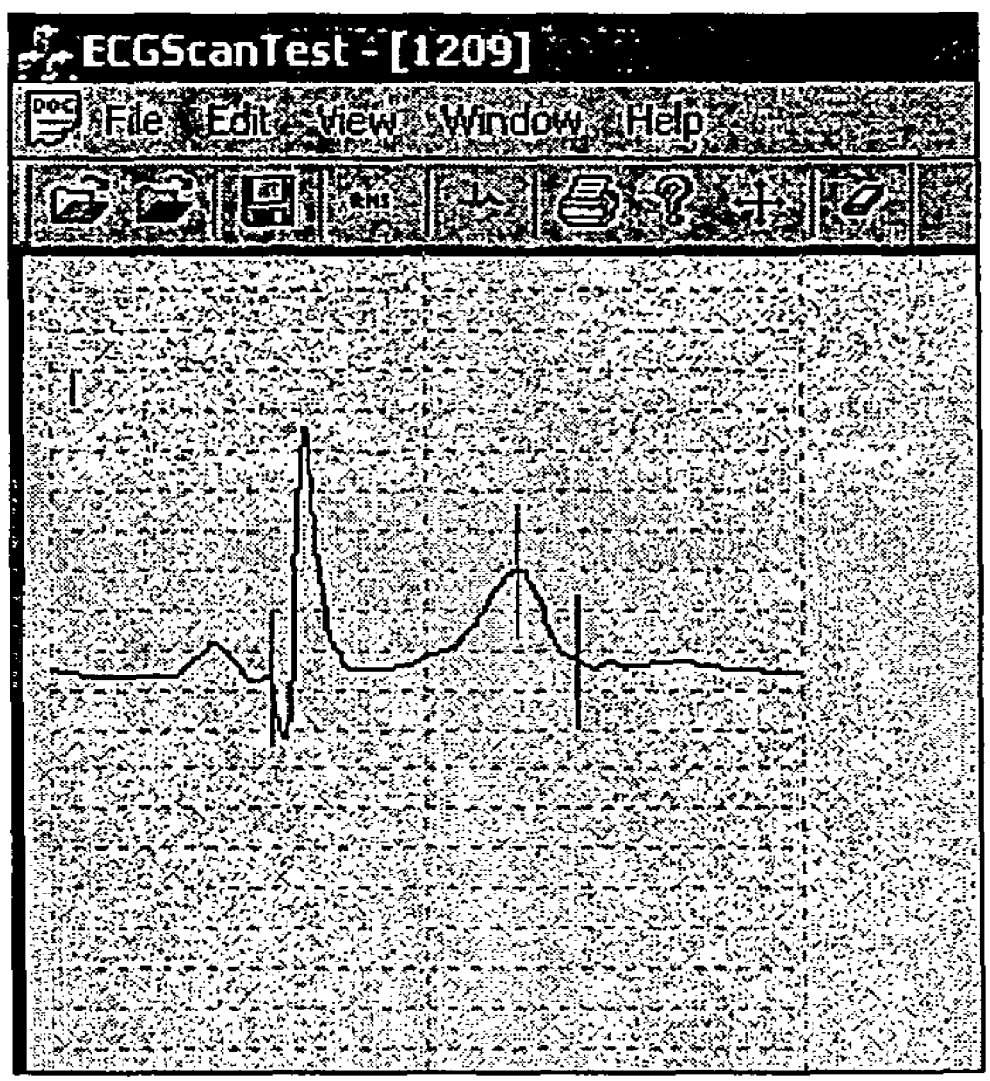
FIG. 9 shows a display used to edit the calipers.

FIG. 9 shows a display used to edit the calipers. The editing process occurred in a blinded mode (i.e. the user could not see/visualize the derived ECG when editing an original and vice-versa). Out of 144 analyzable PQRST complexes, $Q_{ONSET}$ was modified 16 times in an original ECG and 20 times in a derived ECG; $T_{OFFSET}$ was modified 17 times in an original ECG and 16 times in a derived ECG.

Figure 10:
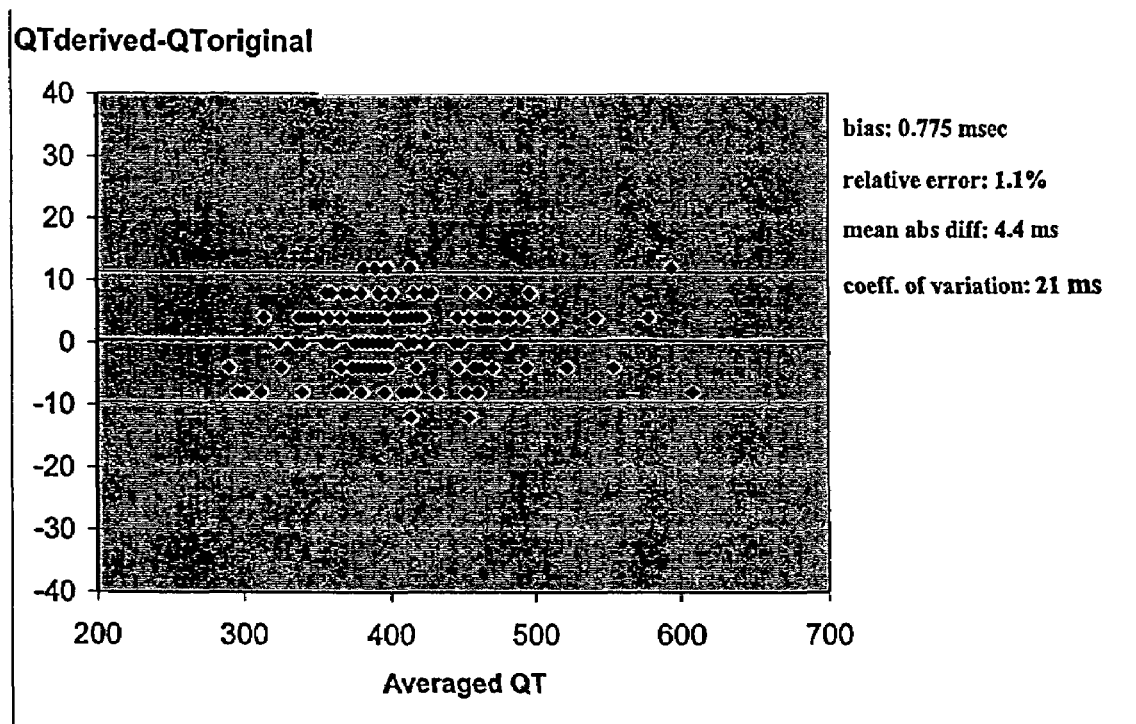
FIG. 10 shows a Bland-Altman plot of QT intervals as measured on the original and derived ECG waves.

Table 2 summarizes the results over the 144 analyzed complexes whereas FIG. 10 is the Bland-Altman plot of the QT intervals as measured on original and derived sequences. The mean difference between QT intervals is less than 1 millivolt. A paired t-test run on the QT intervals indicated non-significant differences in the QT intervals measured on original and on derived ECGs (p>0.1).

TABLE 2

| n = 144 | QT orig | QT derived | Δ QT (der. − orig) |
|---------|---------|------------|---------------------|
| Mean    | 404     | 405        | 0.755               |
| SD      | 55.7    | 56         | 5.41                |
| Min     | 292     | 288        | −12                 |
| Max     | 612     | 604        | 12                  |

It should be particularly noted that, although obtained with common conditions (paper ECG printouts at standard speed and gain, scanning resolution of 300 DPI), the favorable test results discussed herein cannot be extrapolated to conditions different from those imposed in the tests. One problem in performing such comparisons is that an ECG reproduced on paper may deviate from the original digital ECG. If this is the case, the comparison between original and derived ECG may already be biased by a factor independent of the method of the present invention. Indeed, the drawing process of high-frequency portions of the ECG (Q and R waves) can sometimes produce smaller peaks that would determine large sample-by-sample comparisons.

Figure 11:
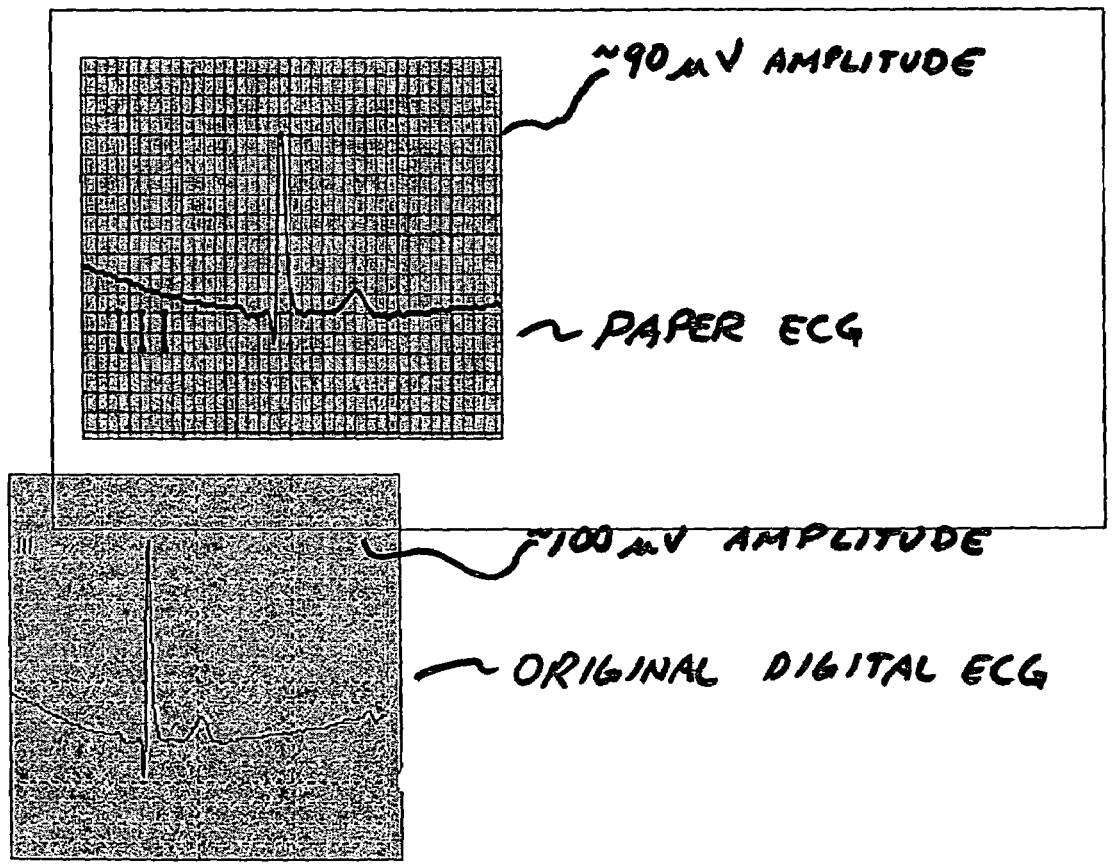
FIG. 11 shows an example of how a paper printout of an original ECG can deviate from the original digital ECG.

FIG. 11 shows one example (from our validation database) where the difference between original and paper ECGs is apparent. More particularly, there is shown a loss in the amplitude of the R and Q waves between the original digital ECG and the paper ECG. In both waves, the vertical distance between horizontal grid lines is 10 microvolts. In the digital ECG the amplitude of the R wave is approximately 100 microvolts, whereas in the paper ECG the amplitude of the R wave is approximately 900 microvolts. Thus, there will be a reduction of approximately 10% in the R wave amplitude in a digitized ECG produced by the method of the present invention using the paper chart. The Q wave, which is particularly sharp in this example, also shows some reduction in amplitude. In the original ECG the Q wave amplitude is slightly less than 200 microvolts whereas on the paper ECG the Q wave amplitude is approximately 150 microvolts. The T wave, however, is reproduced correctly.

Based on the foregoing, the slightly larger absolute value of MeanΔ of Table 1, is likely due to a more direct effect of outliners present in the ECGs showing the loss of R and/or Q wave amplitudes. The individual sample-by-sample delta could be as large as 100 microvolts in extreme cases. Based on this observation, measurements of amplitudes as performed on either paper ECG printouts or on their derived digitized counterparts may sometimes underestimate the real amplitude values of the original ECG.

The present invention provides a method by which paper printouts of an ECG or a computer-readable image file of a scanned paper printout of an ECG are digitized in a manner that provides a derived/digitized ECG that closely reflects the original ECG. Results are positive both in terms of sample-to-sample comparisons and in terms of QT measurements performed on the original and derived ECGs. The inconsistencies found appear to be independent of the method of the present invention, and rather are attributable to direct effects of the internal cardiograph system that created the paper printouts which can cause a reduction of peaks in high-frequency waves (R waves and Q waves). These differences do not appear to affect the measurement of QT intervals, although improved results (smaller coefficient of variation) can be obtained when comparing QT measurements as performed on paper ECGs and on derived digitized ECGs (using on-screen tools).

What is claimed is:

1. A method for digitizing a two-dimensional ECG chart, comprising:
    scanning the ECG chart, said ECG chart including an ECG wave, the ECG wave appearing on a background grid, the grid having generally horizontal and generally vertical grid lines;
    detecting the background grid;
    determining the number of pixels between grid lines; and
    scaling a vertical axis of the scanned ECG chart in units of volts per pixel and scaling a horizontal axis of the scanned ECG chart in units of time per pixel.

2. The method of claim 1, comprising the further step of detecting and correcting for tilt in the grid lines.

3. The method of claim 1, comprising the further step of finding the location of each image pixel relative to the vertical axis as a function of the position of that image pixel relative to the horizontal axis.

4. The method of claim 3, wherein the location of each image pixel relative to the vertical axis represents a voltage value and the location of each image pixel relative to the horizontal axis represents a time value.

5. The method of claim 4, comprising the further step of storing data corresponding to the voltage of each image pixel as a function of time.

6. A computerized method of deriving a digital ECG waveform from a computer readable-file representing an optically-scanned ECG chart, said method comprising the processes of:
    opening the computer readable-file representing the ECG chart;
    displaying an image of the ECG chart;
    selecting a portion of the displayed image of the ECG chart;
    characterizing the displayed image;
    detecting a plurality of grid lines appearing on the displayed image and being generally oriented in the horizontal and vertical directions; and
    extracting and digitizing the ECG waveform appearing on the displayed image.

7. The method of claim 6, wherein said characterizing process comprises at least one of inputting, selecting and confirming characteristics of the ECG chart corresponding to the displayed image.

8. The method of claim 7, wherein said characteristics include one or more of paper speed and gain at which the ECG chart corresponding to the displayed image was produced, and the resolution with which the ECG chart corresponding to the displayed image was scanned.

9. The method of claim 6, wherein said detecting a plurality of grid lines comprises one of a manual mode, a range mode, and an exact mode.

10. The method of claim 9, wherein said manual mode comprises at least one of inputting, selecting and confirming input parameters of the ECG chart corresponding to the displayed image.

11. The method of claim 10, wherein said input parameters include the paper speed at which the ECG chart corresponding to the displayed image was produced, the resolution with which the ECG chart corresponding to the displayed image was scanned, and the time interval represented by the distance between adjacent grid lines on the ECG chart corresponding to the displayed image.

12. The method of claim 11, comprising the further process of mathematically deriving the distance in pixel units between adjacent grid lines.

13. The method of claim 9, wherein said range mode comprises inputting a tolerance range for said detecting process.

14. The method of claim 9, wherein said manual mode comprises selecting a region of the displayed image that includes a plurality of grid lines in each of the horizontal and vertical directions.

15. The method of claim 6, further comprising the process of displaying one or more of the number of pixels between grid lines, the angle of the grid lines, and the reliability of the detecting process.

16. The method of claim 6, wherein said extracting and digitizing process comprises:
    selecting a region of the displayed image including at least a portion of the ECG waveform; applying a computer algorithm embodying an active contour and dynamic programming approach to derive a digitized ECG waveform.

17. The method of claim 16, wherein said applying process includes representing the ECG waveform with an active contour having a vertical value corresponding to each horizontal pixel location within the selected region.

18. The method of claim 17, wherein said applying process further comprises defining a cost function for at least the portion of the displayed ECG waveform within the selected region.

19. The method of claim 18, wherein the solution to the cost function corresponds to a digital representation the displayed ECG waveform.

20. A system for deriving a digital ECG waveform, comprising:
- a computer having a display, at least one storage device, memory, and at least one input device;
- application software executable by said computer and being at least one of accessible to said computer and stored in said storage device or said memory of said computer, said application software configured for deriving a digital ECG waveform based upon an optically-scanned ECG chart;
- an opening module enabling a user to open and display on said display the optically-scanned ECG chart;
- a selecting module enabling a user to select a portion of the displayed image of the ECG chart;
- a characterizing module enabling a user to characterize the displayed image;
- a detecting module for detecting a plurality of grid lines appearing on the displayed image in both the horizontal and vertical directions; and
- an extracting and digitizing module for extracting and digitizing the ECG waveform appearing on the displayed image.

* * * * *